(12) United States Patent
Panin (10) Patent No.: US 9,044,153 B2
(45) Date of Patent: Jun. 2, 2015

(54) RANDOM SINOGRAM VARIANCE REDUCTION IN CONTINUOUS BED MOTION ACQUISITION

(71) Applicant: Vladimir Y. Panin, Knoxville, TN (US)

(72) Inventor: Vladimir Y. Panin, Knoxville, TN (US)

(73) Assignee: Siemens Medical Solutions USA, Inc., Malvern, PA (US)

(\*) Notice: Subject to any disclaimer, the term of this patent is extended or adjusted under 35 U.S.C. 154(b) by 172 days.

(21) Appl. No.: 13/737,437

(22) Filed: Jan. 9, 2013

(65) Prior Publication Data

US 2014/0194735 A1 Jul. 10, 2014

(51) Int. Cl.
*A61B 6/00* (2006.01)
*A61B 6/03* (2006.01)
*G06T 11/00* (2006.01)
*G01T 1/163* (2006.01)

(52) U.S. Cl.
CPC ............... *A61B 6/037* (2013.01); *G01T 1/1635* (2013.01); *A61B 6/5205* (2013.01); *A61B 6/5258* (2013.01); *G06T 11/003* (2013.01)

(58) Field of Classification Search
USPC ...................................... 600/436; 250/363.04
See application file for complete search history.

(56) References Cited

U.S. PATENT DOCUMENTS

2010/0057819 A1\* 3/2010 Panin ............................ 708/203

OTHER PUBLICATIONS

Brasse et al. "Correction Methods for Random Coincidences in Fully 3D Whole-Body PET: Impact on Data and Image Quality". J Nucl Med. 2005;46:859-867.\*
Badawi et al. "Randoms variance reduction in 3D PET". Phys. Med. Biol. 44 (1999) 941-954.\*
Panin, V.Y. "Accurate Estimation of Single Counts from Axially Compressed Random Data". Nuclear Science Symposium Conference Record, 2006. IEEE , vol. 5, No., pp. 2796,2800, Oct. 29, 2006-Nov. 1, 2006.\*
Yang et al. "A New Axial Smoothing Method Based on Elastic Mapping". IEEE Transactions on Nuclear Science, vol. 43, No. 6, Dec. 1996.\*
M. Dahlbom et al., "Implementation of True Continuous Bed Motion in 2-D and 3-D Whole-Body PET Scanning," IEEE Trans. Nucl. Sci. 48, pp. 1465-1469, 2001.
M.E. Casey et al.,"A component based method for normalization in volumePET," In: Proceedings of the 3rd International Meeting on Fully Three-Dimensional Image Reconstruction in Radiology and Nuclear Medicine, Aix-les-Bains, France, pp. 67-71, 1995.
V.Y. Panin, "Iterative algorithms for variance reduction on compressed sinogram random coincidences in PET," 2008 IEEE Nucl. Sci. Symp. and Med. Imag. Conf., pp. 3719-3725, Dresden, Germany.

\* cited by examiner

*Primary Examiner* — Unsu Jung
*Assistant Examiner* — Phong K Huynh
(74) *Attorney, Agent, or Firm* — Peter Kendall (57) ABSTRACT

Random sinogram variance is reduced in continuous bed motion acquisition. The randoms are modeled as a product of transverse singles efficiencies. The random sinogram is assumed to be a smooth function in the axial direction, collapsing the parameterization for estimating the transverse singles efficiencies into a single, conceptual ring. By solving the product, the mean random values are used to smooth the randoms in image reconstruction with less noise and artifacts.

21 Claims, 3 Drawing Sheets

RANDOM SINOGRAM VARIANCE REDUCTION IN CONTINUOUS BED MOTION ACQUISITION

BACKGROUND

The present embodiments relate to positron emission tomography (PET).

PET systems and corresponding detectors have a limited field of view. Typically, the entire patient cannot be scanned with the patient in one position. In a step and shoot (S&S) approach to scan a greater portion of the patient, the patient is moved between sequential scans, but remains stationary for each of the scans. However, the gaps between blocks of detectors cause a drop in axial sensitivity when assembling the different scans for segment zero (2D) acquisitions. For three-dimensional (3D) acquisition, greater axial uniformity may be provided for S&S. Low sensitivity spots of various segments are mixed in image space, and therefore the loss of sensitivity only occurs in the end planes.

Continuous bed motion (CBM) acquisition performs a scan of the patient while the patient is moving through the PET system. CBM may improve the axial uniformity of PET images over S&S for 2D acquisitions. For 3D acquisitions, CBM acquisition may result in super-resolution images by oversampling the image in the axial direction. However, this advantage may not be applicable in the case of patient scanners, where effective resolution is relatively low due to high level noise using short clinical scans. One particular source of noise is noise in randoms or delayed coincidence. Both S&S and CBM acquisition reconstruction use a mean value of randoms events.

The expected randoms rate is used in Poisson model iterative image reconstruction. The expected randoms contribution to line-of-response (LOR) data may be estimated from the crystal singles rate, according to the randoms rate equation:

$$\bar{r}_{ij} = 2\tau s_i s_j, \quad (1)$$

where indexes i and j denote crystals in coincidence, $s_i$ is the mean single rate for a given crystal i, and $2\tau$ is the coincidence time window.

The random count may be measured on the crystal level from the singles rates. However, some systems may acquire randoms (delay) projection data separately and not measure the crystal singles rate. The direct use of these noisy randoms measurements in the image reconstruction may lead to artifacts and increased image noise levels. The variance reduction of measured delayed coincidence sinograms may be performed through singles rate estimations from these data, followed by the construction of a mean random sinogram.

However, CBM acquisition significantly complicates this variance reduction. CBM causes summation over all detector pairs ij in the axial direction so that a per crystal singles rate cannot be determined. Further, the singles rate s is not constant and is a function of time due to the various activity parts of the patient as the patient passes through the field of view of the scanner. The result is an increase in the number of unknowns, complicating direct estimation of singles as function of time.

BRIEF SUMMARY

By way of introduction, the preferred embodiments described below include methods, systems, and non-transitory computer readable media for random sinogram variance reduction in continuous bed motion acquisition. The randoms are modeled as a product of transverse singles efficiencies. The random sinogram is assumed to be a smooth function in the axial direction, collapsing the parameterization for estimating the singles efficiencies into a single, conceptual ring. By solving the product, the constructed mean random values are used for reconstruction with less noise and artifacts. The product is solved first, so efficiencies are estimated. Then, efficiencies are multiplied back to produce randoms. Since the number of efficiencies are less than number of equation for randoms, this multiplication does not give back the original value for each random value.

In a first aspect, a method is provided for random sinogram variance reduction in continuous bed motion acquisition. A positron emission tomography (PET) scanner having a plurality of rings of detectors acquires line-of-response events from a patient while the patient is moving in the PET scanner. At least some of the line-of-response events include random contribution. The random contribution is modeled as a product of transverse singles efficiencies with the plurality ring detectors treated as one ring along an axial direction. Variance of the random contribution is reduced as a function of the modeling. An image of the patient is reconstructed as a function of the reducing.

In a second aspect, a non-transitory computer readable storage medium has stored therein data representing instructions executable by a programmed processor for random sinogram variance reduction in continuous bed motion acquisition. The storage medium includes instructions for decomposing sinogram plane randoms into two-dimensional transverse efficiencies, where the two-dimensional transverse efficiencies are transverse to an axial dimension and the sinogram plane randoms correspond to the continuous bed motion acquisition, solving for a mean random sinogram from the transverse efficiencies, and smoothing variance of the sinogram plane randoms in the axial dimension as a function of the mean random sinogram.

In a third aspect, a system is provided for random sinogram variance reduction in continuous bed motion acquisition. A bed is configured to move during a positron emission tomography (PET) scan. Rings of axially spaced detectors are operable to perform the PET scan while the bed moves. A processor connects to the detectors. The processor is configured to constrain random contribution to line-of-response events as a function of a product of efficiencies of the detectors. The product is of efficiencies transverse to an axial dimension.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Random sinogram variance is reduced for continuous bed motion (CBM) positron emission tomography (PET). For CBM reconstruction, projection data is modeled as sum of components, where one component is the mean random. The mean random is used during reconstruction. In particular, the variance in random information as opposed to true coincidence events defining a line-of-response is smoothed. To smooth, the randoms are modeled as transverse efficiencies, providing averaging over axial planes quantities. Modeling errors in the axial direction may be suppressed in CBM using the modeling.

Figure 1:
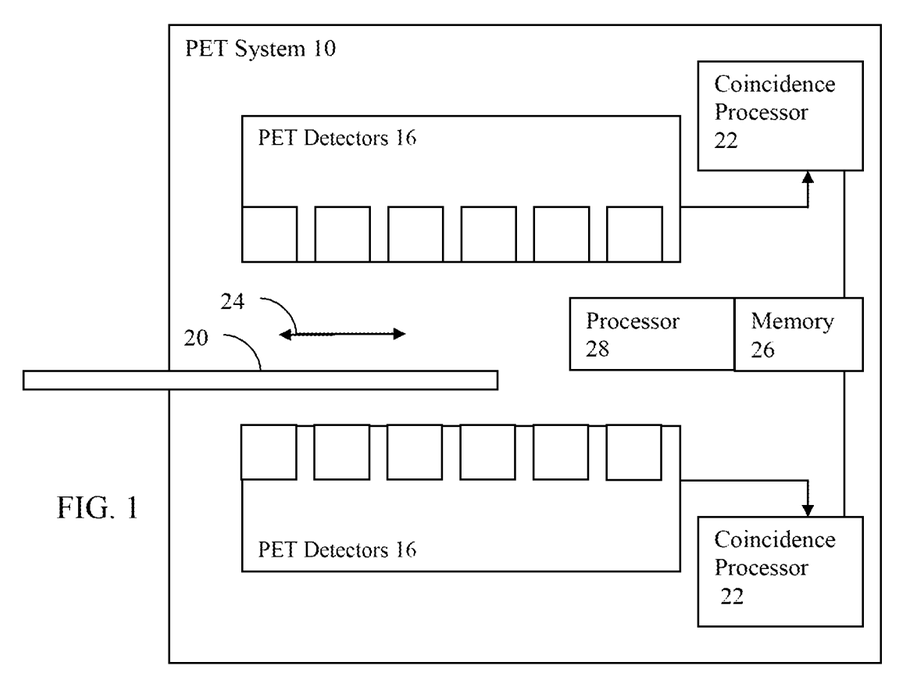
FIG. 1 is a block diagram of a system, according to one embodiment, for random sinogram variance reduction in continuous bed motion acquisition.

FIG. 1 shows a PET system 10 for random sinogram variance reduction in continuous bed motion acquisition. The PET system 10 includes rings of detectors 16, a bed 20, coincidence processors 22, a memory 26, and a processor 28. The processor 28, memory 26, and/or a display are part of the PET system 10 or are separate (e.g., a computer or workstation). Additional, different, or fewer components may be provided. For example, the system is a computer without the detectors 16 and bed 20, instead relying on data acquired by a separate scanner. As another example, the PET system 10 includes power supplies, communications systems, and user interface systems.

The bed 20 is a gurney, table, or other support to hold an examination subject such as a patient. A robot, gears, cable, track, and/or other device moves the bed 20. The movement is along an axial dimension represented by double arrow 24. The detectors 16 and/or PET scanner 10 form a bore or hollow cylinder through which the bed 20 moves the patient. The distance from the axial axis is the radial distance. The angle about the axial axis is the azimuth. Other coordinate systems than a cylindrical or polar coordinate may be used.

The movement is continuous, at least during part of the scanning. The bed 20, while supporting the patient, is moved at a same or a varying velocity along the axial dimension 24. The movement may pass the patient through the bore or merely partly into the bore. The movement is with or without acceleration. In one embodiment, the movement is back and forth, scanning the patient multiple times in a cyclical pattern. A single pass may be used in other embodiments.

The movement occurs during scanning (e.g., detection or measurement) by the detectors 16. The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

Figure 2:
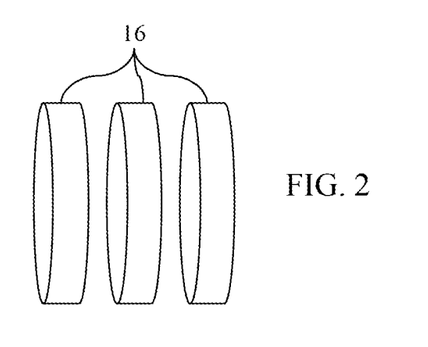
FIG. 2 shows example rings of detectors.

The detectors 16 are arranged individually or in groups. Blocks or groups of detectors 16 are arranged in any pattern around the bore. FIG. 2 represents blocks of detectors 16 arranged as separate rings around the bore. The rings are shown spaced apart, but are placed adjacent or abutting each other. Any gap may be provided between blocks within a ring, detectors within a block, and/or between rings. Any number of detectors in a block, detector blocks in a ring, and/or rings may be used. The separate detectors 16 of each ring have their own singles rate and/or efficiency.

The PET system 10 is a nuclear imaging system. The detectors 16 detect gamma rays emitted indirectly by a positron-emitting tracer. Pairs of gamma rays generated by a same positron may be detected using the ring of the detectors 16. The pairs of gamma rays travel about 180 degrees apart. If the direction of travel intersects the arrangement of detectors 16 at two locations, a coincident pair may be detected. To distinguish specific pairs, the coincidence of detected gamma rays is determined. The timing of receipt is used to pair the detected gamma rays. If the direction of travel intersects only one detector, a random may be detected. The detectors 16, for a given coincidence sample period, may detect gamma rays associated with both coincidence and randoms. With sufficient frequency, these randoms cause noise for coincidence processing.

As the bed 20 moves, the patient passes through the rings. A given part (e.g., organ) of the patient is within different rings at different times due to the continuous bed motion. The line-of-responses for the same part of the patient and corresponding actual three-dimensional location (i.e., point along the line-of-response) is at different locations at different times. The detectors 16 continue to detect gamma rays as the bed 20 and patient moves so different lines-of-response may be for the part at different positions within the bore.

Each individual detection output from the detectors 16 includes energy, position, and timing information. Alternatively, the detectors 16 output energy information and a receiving processor determines the timing and position (e.g., based on port assignment or connections). The timing information is used to determine coincidence of detection by different detectors by the coincidence processors 22. Pairs of gamma rays associated with a same positron emission are determined. Based on the detected event, a line-of-response is determined given the detectors involved in the detection of that event. Randoms add noise to the detection of events. The detected events are either true coincidence detections or due to randoms.

The detected events are passed to the memory 26 and/or processor 28. Alternatively, the coincidence processor 22 implements the variance reduction rather than a separate processor 28. The processor 28 connects with the detectors 16, such as through the coincidence processors 22.

The processor 28 is a general processor, digital signal processor, graphics processing unit, application specific integrated circuit, field programmable gate array, digital circuit, analog circuit, combinations thereof, or other now known or later developed device for processing detected line-of-response events or random data. The processor 28 is a single device, a plurality of devices, or a network. For more than one device, parallel or sequential division of processing may be used. Different devices making up the processor 20 may perform different functions, such as one processor for estimating transverse efficiencies and another processor for reducing variation. In one embodiment, the processor 28 is a control processor or other processor of the PET system 10. In other embodiments, the processor 28 is part of a separate workstation or computer.

The processor 28 operates pursuant to stored instructions to perform various acts described herein, such as estimating transverse efficiencies, determining a mean random sinogram, variance reduction, and/or reconstruction. The processor 28 is configured by software and/or hardware to perform any or all of the acts of FIG. 3.

The operation and configuration of the processor 28 is first described in general below. One example implementation is described in more detail in the following discussion of FIG. 3.

The processor 28 is configured to reduce variance or constrain random contribution to line-of-response events. The random contribution to the sinogram is reduced using a product of efficiencies of the detectors. The sinogram plane randoms are decomposed into the efficiencies. The efficiencies are measured along the transverse direction to the axial dimension. The efficiencies are in the radial and azimuth directions, so are transverse to the axial motion of the patient. The decomposition is performed plane-by-plane. The CBM sinogram includes planes. Each plane belongs to a particular segment of the same polar angle. For each plane, a virtual ring is applied to estimate efficiencies per plane. Therefore, the number of transverse efficiency sets is equal to number of planes in the CBM sinogram. Variance of the random is reduced due to fact that number of bins (LORs and randoms value) in one plane is much larger than number of efficiencies. If the number of efficiencies is N in a virtual ring, then number of LORs is about $N^2$.

The axial response of the efficiencies is treated as a smoothly varying function, so the model uses the transverse efficiencies without separate solution for the axial direction. A single axial ring is modeled. Each plane is a sinogram. The sinogram corresponds to one ring. Therefore, each plane has its own ring with efficiencies. However, the efficiencies should be a smooth function from one plane to the next plane.

The processor 28 iteratively solves for efficiencies from noisy random sinogram plane. The model of the transverse efficiencies, with the detected events, is used to determine a solution for the mean random sinogram as part of solving for the efficiencies. This mean random sinogram is used to constrain the randoms in the detected events. The randoms are smoothed or filtered by preventing the randoms for a given crystal or detector 16 from exceeding the mean. The mean is used in reconstruction. Since it is a mean, not noisy data, the mean produces a less noisy image in reconstruction. This acts as a filtering effect on the image.

For every sinogram bin (LOR), noisy data are replaced by the mean. The mean is obtained from many noisy realization of the sinogram. Since one has only one sinogram, the mean value is modeled. The same is provided in image reconstruction. Trues are noisy. Its mean is projection of some image. In the reconstruction process, the mean is constructed and compared to noisy data. By changing the image, the closest mean data to measured data is found. Randoms smoothing is similar in concept, where the mean is a product of efficiencies. There is no constraint on the randoms in axial direction. Only axial smoothing is applied on mean estimation.

The processor 28 uses the events (e.g., true line-of-response events and randoms) stored in the memory 26 for processing. For processing, the data bypasses the memory 26, is temporarily stored in the memory 26, or is loaded from the memory 26.

The detected events, line-of-response information (e.g., sinograms), model, efficiencies, mean random information, reconstructed image, or other data is stored in the memory 26. The data is stored in any format. The memory 26 is a buffer, cache, RAM, removable media, hard drive, magnetic, optical, database, or other now known or later developed memory. The memory 26 is a single device or group of two or more devices. The memory 26 is part of the PET system 10 or a remote workstation or database, such as a PACS memory.

The memory 26 is additionally or alternatively a non-transitory computer readable storage medium with processing instructions. The memory 26 stores data representing instructions executable by the programmed processor 28 for random sinogram variance reduction in continuous bed motion acquisition. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The PET system 10 may include a display. For example, the processor 28 reconstructs the patient or object being scanned from the line-of-response information after random constraint or filtering. The reconstruction is used for three-dimensional rendering, multi-planar reconstruction, or two-dimensional imaging of the function of the object or patient. The images are displayed on the display. The display is a CRT, LCD, plasma screen, projector, printer, or other output device for showing an image.

Figure 3:
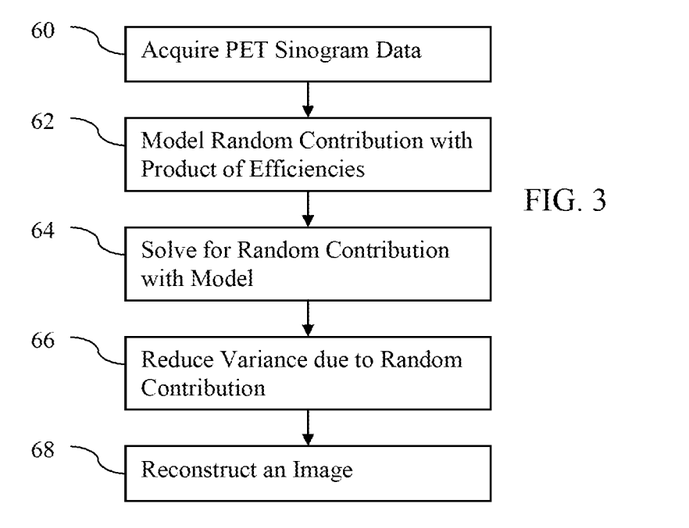
FIG. 3 is a flow chart of an embodiment of a method for random sinogram variance reduction in continuous bed motion acquisition.

FIG. 3 shows a method for random sinogram variance reduction in continuous bed motion acquisition. The method of FIG. 3 is implemented by the processor 28, the PET system 10, or other component or system. Additional, different, or fewer acts may be performed. The acts are performed in the order shown or a different order.

In act 60, PET sinogram data is acquired. The acquisition is by scanning with the PET system. In alternative embodiments, the acquisition is by transfer or upload from a memory.

Line-of-response events from a patient are detected while the patient is moving in the PET scanner. The acquisition occurs over any period. For example, the acquisition is over 1, 10, 100, or other number of minutes.

The bed is moving the patient during that time. The movement is over any range of motion, such as for scanning all or only a part of the patient. The bed may move cyclically during the period, such as moving back and fourth once, five times, ten times, twenty times, forty times, or other number of times. Alternatively, the bed moves in one direction only during the scan.

The motion of the bed is continuous over at least a portion of the acquisition period. With cyclical motion, there may be one or two times of no motion and parts of the period with acceleration or deceleration. In alternative embodiments, a constant velocity is provided.

During the continuous bed motion, gamma rays are detected by one or more rings of detectors or other grouping of detectors. The same detectors are used to detect positron-electron annihilations from different parts of the patient. Due to the motion, annihilations in a same part of the patient may be detected at different rings at different times even where the line of gamma ray propagation is the same relative to the patient for each time. Of course, the line of propagation may be different at different times for a same location of the patient.

For axial sampling, reconstruction time requirements may dictate the same CBM axial sampling (e.g., about 2 mm due to crystal pixel size) as in S&S acquisition. Other axial sampling may be used. Due to the motion of the bed during acquisition, a CBM acquisition leads to additional axial blurring. A small (i.e. smaller than an image pixel) object is effectively distributed across the whole pixel due to motion instead of staying at the pixel center, for example. On the other hand, finer (e.g., significantly less than 2 mm) CBM sampling may lead to potentially better axial resolution compared to S&S due to oversampling. Where the detector response width is significantly large as compared to the axial pixel size, less improvement may occur from oversampling. Table I provides a Fourier rebinning filtered back projection (FORE+FBP) resolution assessment of about a 0.1 mm size F-18 point source acquired with 1 mm/s bed speed. Table 1 shows full width at half maximum (FWHM) in mm of a point source with varying CBM axial sampling.

|  | CBM, 2 mm | CBM, 0.5 mm | S&S, 2 mm |
|---|---|---|---|
| Radial | 4.41 | 4.34 | 4.36 |
| Tangential | 4.36 | 4.35 | 4.36 |
| Axial | 4.95 | 4.21 | 4.51 |

The transverse resolution may not degrade in the CBM acquisition, proving that the bed movement vector is aligned with the axial scanner axis. To compare resolution measurements, the data is normalized. In CBM, the oblique segment has lower weight when comparing to S&S due to less scanning time. Normalization-free FORE+FBP reconstruction produces results biased toward segment zero resolution in CBM data, where there is no axial FORE interpolation. The non-normalized bias toward segment zero of FORE+FBP reconstruction may result in better axial resolution, which may partially offset the loss of axial resolution in CBM due to the bed motion.

The scanning with continuous bed motion acquires detected emission events for functional information. The detected gamma rays are checked for coincidence to define lines-of-response. Any time window may be used for coincidence processing, such as 0.2 microsecond coincidence time window (e.g., PET may use about a 5 nanoseconds window). Each detected emission event corresponds to a line or part of a line through a patient. By detecting emission events from different angles around a patient, a volume may be reconstructed. The resulting line-of-response events may include noise from randoms. Randoms may be called noise, but are rather additional background contribution. At least some of the line-of-response events of the sinogram are contributions from randoms.

To accommodate for the contribution from randoms in the reconstruction, the random mean is modeled in act 62. The random contribution is modeled as a product of transverse singles efficiencies. As noted above, the random contribution may be modeled from the crystal singles rate. The expected randoms contribution of line-of-response (LOR) is modeled according to the randoms rate equation:

$$\bar{r}_{ij} = 2\tau s_i s_j, \quad (1)$$

where s is the mean single rate for a given crystal i or j, and $2\tau$ is the coincidence time window. This model (equation 1) represents a set of nonlinear equations where there is no need to separately estimate the multiplication constant $2\tau$. The singles rate may be redefined as $s_i = \sqrt{2\tau} s_i$.

As noted above, using the singles crystal rate may not be appropriate for CBM acquisition. Another concern is compression used in the detected events. In a clinical environment, data are acquired with some type of compression to reduce the data size. Given N crystals or detectors, there are $N^2$ combinations or lines-of-response that are possible. To compress, lines-of-response with similar angles (e.g., adjacent detectors or crystals) are binned together despite being from different detector pairs.

One or more types of compression may be used. For example, axial (span) compression is used. In axial compression, the number of oblique planes is significantly reduced by combining the lines-of-response of similar polar angles. As another example, trans-axial mashing is used. In trans-axial mashing, the number of sinogram views is reduced by combining the lines-of-response of adjacent azimuth angles. Other compressions or combinations of both may be used.

Such compression complicates the basic random equation (equation 1) by summation over different lines-of-response. The grouping of different lines from different detectors into the same bin makes solving for singles rates associated with specific detectors difficult.

One solution for dealing with compression models the random data rate as a Poisson variable. An iterative algorithm is used to estimate singles and the mean randoms contribution where compression is used. Assuming that the line-of-response randoms data rate, $r_{ij}$, is a Poisson variable, the randoms equation for the mean value of compressed data is:

$$\bar{r}_{\rho,\theta,\zeta} = \sum_{i,j} \frac{\omega_{\rho\theta\zeta,ij}}{2} s_i s_j, \quad \omega_{\rho\theta\zeta,ij} = \begin{cases} 1, & ij \text{ contribute to } (\rho, \theta, \zeta) \\ 0, & \text{otherwise} \end{cases} \quad (2)$$

where the data is parameterized by the sinogram index $\rho$ (radial), $\theta$ (azimuth), and $\zeta$ (axial, including polar angle), and $\omega$ is the ij line-of-response contribution factor to the sinogram bin. The model estimates all s values from all randoms data, taking into account Poisson statistics. The variance reduction randoms data are constructed using the model where CBM does not complicate the iterative solution.

For CBM, the randoms data rate is also modeled as a Poisson variable. The random contribution to the line-of-response events is modeled as a Poisson variable. Other distributions than Poisson may be used to the model the sinogram plane randoms.

The CBM acquisition may be modeled with the singles rate as:

$$\bar{r}_{\rho,\theta,\zeta}^{CBM} = \int \sum_{i(t),j(t)} \frac{\omega_{\rho\theta\zeta,i(t)j(t)}}{2} s_i(t) s_j(t) dt \quad (3)$$

where the summation is over all detectors pairs ij in the axial direction and the singles rate s is not constant (is a function of time) due to the various activity parts of the object as the object passes through the FOV of the scanner. The number of unknowns is increased as compared to equation 2 and direct estimation of singles as function of time may be a complicated task.

Transverse efficiencies are used instead of singles to model the randoms data rate. The plurality of ring detectors is treated as one ring along an axial direction. The random contribution of the sinogram planes is decomposed into the transverse singles efficiencies where transverse is transverse to the axial direction (i.e., radial and azimuth contribution is modeled). Using transverse efficiencies, the detector pairs for the random contribution are mapped to one virtual ring, providing two-dimensional transverse efficiencies in polar coordinates. In transverse, the detectors are distinguishable.

Assuming that an averaging effect may be achieved by decomposing each sinogram plane randoms into transverse efficiencies simplifies the solution. Such efficiencies accommodate for detector efficiencies (e.g., detector edge efficiency is lower compared to the efficiency of the central part of the detector) and geometrical effect, where singles distribution varies due to differences in attenuation. The model and corresponding equation is the same in form, but the detector pair ij always belongs to the one virtual ring, corresponding to a particular sinogram plane. One plane has its own virtual ring. There is axial dependency still. Efficiencies are axial dependent.

The randoms decomposition is performed plane-by-plane in the sinogram domain:

$$\bar{r}_{\rho,\theta,\zeta} = \sum_{i,j} \frac{\omega_{\rho\theta,ij}}{2} \varepsilon_i(\zeta)\varepsilon_j(\zeta) \quad (4)$$

This formulation accounts for compression using parameters defined in the radial and azimuth dimensions and not the axial dimension. The radial and azimuth indexes are used for the detector contribution factor, with the transverse efficiencies being a function of the axial dimension. The transverse efficiencies are defined with the radial and azimuth indexes. The random contribution is a sum of a product of the transversely spaced pairs of the detectors within a sinogram bin. The decomposition is plane-by-plane in a sinogram domain. Other models using transverse efficiencies may be used.

In act 64, the model using transverse efficiency (e.g., equation 4) is used to solve for the random contribution. The line-of-response data or sinograms are used with the model to iteratively solve for the mean random sinogram. Randoms are acquired as a separate sinogram. There are two sinograms: prompt and delayed. The delayed sinogram contains the randoms, so the model is used to smooth this delayed sinogram. The transverse efficiencies are estimated iteratively by the random decomposition. The result of the solution is a mean randoms rate or sinogram.

The mean random rate represents an amount of randoms for each detector. The mean for each pair of detectors (LOR, sinogram bin) may be different. A randoms rate for a given detector above the mean is likely to be noise.

In act 66, the variance in the line-of-response events due to randoms contribution is reduced. The constraint is applied prior to reconstruction. Variance is not reduced in prompt (i.e., trues plus randoms) sinogram. Variance is modeled in image reconstruction. The mean (expected) randoms are used in image reconstruction, replacing the original randoms sinogram. Random smoothing is done before image reconstruction. The mean value per LOR is estimated. In filtering, mean is estimated assuming that neighboring bin value should be of similar values. Here, different modeling is used to get rid of variance from acquisition to acquisition.

Separate means are provided for each different detector or detector pair. The different means are applied to constrain the line-of-response associated with the corresponding detectors. The mean may alternatively be by segment. Any number of segments may be used.

By constraining the random contribution with the mean, the variance is reduced. The variance of the sinogram plane randoms is smoothed as a function of the mean random sinogram. The smoothing occurs in the transverse segment.

Since the modeling is performed plane-by-plane in the axial direction, the constraint may not smooth in the axial direction. Due to the nature of CBM, the randoms data should be smooth in the axial direction in the sinogram segment. This provides an opportunity to smooth the mean randoms estimation in the axial direction. This smoothing is performed inside the sinogram segment. The mean random sinogram has axial direction. Just axial filtering is performed in this direction for each segment. Segments are axially independent. The mean random sinogram is used for axial smoothing. The virtual ring is divided into slices spaced axially. The random contribution is scaled for the number of slices. For example, the average or mean random contribution is divided by the number of slices and the result is used as the constraint for axial smoothing. This restores the axial efficiency from the transverse singles efficiencies, providing reduction of the axial variance.

Figure 4:
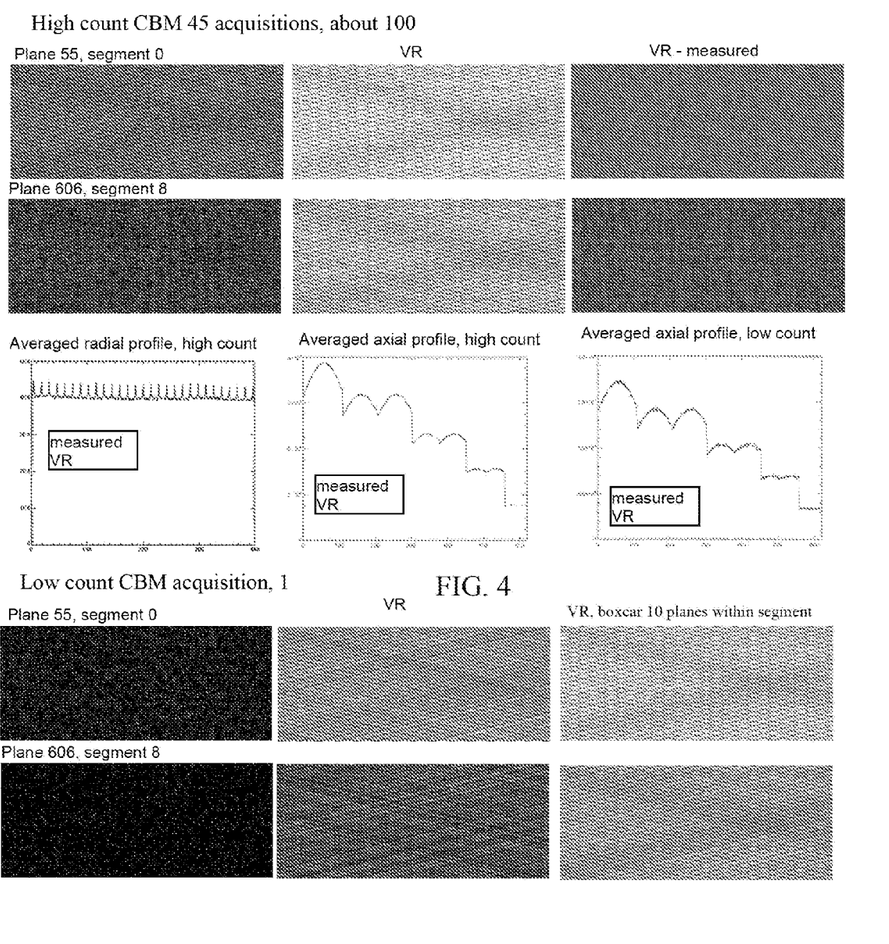
FIG. 4 shows images and profiles demonstrating performance of CBM with variance reduction using a NEMA IQ phantom.

FIG. 4 shows use of the transverse efficiencies for constraining randoms contribution in continuous bed motion acquisition. A Ge-68 phantom (NEMA IQ) is repeatedly scanned (45 times) in CBM mode. A high count random sinogram Is obtained by summing all acquisitions (i.e., sum of the data from the 45 repetitions). The sinogram data is shown for two different planes where each plane is for a different segment. For the high count, the left most images show the data prior to smoothing using the transverse efficiencies. The center images (VR) show the data after smoothing. The right images (VR-measured) show the difference or removed randoms noise.

The lower set of six images shows the results for a low count rate. The low count rate randoms sinogram represents just one such acquisition (i.e., only sinogram data from one of the 45 repetitions is used). The variance reduction appears to not lead to bias in the random sinograms. Instead of showing extracted noise, the right images for the low count rate show filtering across planes. A ten plane boxcar filter is used, but other filtering and/or number of planes may be used. Axial smoothing by any number of planes (e.g., ten planes or 2 cm) may improve performance of variance reduction procedure in the case of a low count scan.

Graphs of the measured profile of random mean for the high count example are shown for both radial and axial directions. In the radial direction, the mean is shown as having higher frequency variation as a function of radial offset due to block structure. In the axial direction, the profile is shown as a function of plane where the profile has distinct regions due to segments. Both profiles are an average where the radial profile is averaged over the axial direction and the axial profile is averaged over the axial direction.

The axial profile is shown for the low count case as well. The axial profile for the low count case shows higher frequency variation due to the greater noise associated with the low count as compared to the higher count example.

In act 68, an image is reconstructed from the line-of-response data. The image is of the patient, such as PET image showing function or uptake of the radiopharmaceutical. The line-of-response data used for reconstruction is output from the reduction, so has random contribution that is constrained by the mean based on the transverse efficiencies. The image benefits from the reduction of the variance of the random contribution.

Any reconstruction may be used. In one embodiment, the reconstruction is a Poisson iterative reconstruction. OSEM, FORE, or other reconstructions may be used. The reconstruction estimates the object or patient space from the lines-of-response. The detected events are used to iteratively determine using forward, backward, or forward and backward projection.

The reconstruction accounts for the continuous bed motion. Chunking may be used in the reconstruction. Clinical reconstruction requirements (e.g. image should be available after acquisition with smallest possible delay) lead to reconstruction of the continuous bed motion sinogram in parts or "chunks." Any reconstructed part (chunk) size may be used. Large overlapping of chunks may not lead to loss in counts, but redundancy in reconstruction. Chunk size may be increased at the expense of reconstruction delay after scanning. In one embodiment, the chunk size and chunk overlap are chosen to match S&S acquisition.

There is no change in scatter correction in transition from S&S to CBM. Scatter is estimated for each chunk. While scatter estimation suffers from unknown activity outside the field of view, scatter scaling is performed to overcome this problem. Scaling in principle should be the same procedure for CBM acquisition. Nevertheless, more uniform axial scatter estimation may result in CBM as compared to S&S. This result is likely due to fact that scatter scaling is performed on segment zero data only, where S&S acquisition demonstrated axial non-uniformity.

The reconstructed volumes may be output for storage. Alternatively, one or more images of the reconstructed volume are displayed. Any functional, anatomical, or functional and anatomical imaging may be used. Cross sections of the volume may be mapped to display values. The volumes may be rendered, such as using surface or projection rendering, from one or more viewing directions.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for random sinogram variance reduction in continuous bed motion acquisition, the method comprising:
    acquiring, with a positron emission tomography (PET) scanner having a plurality of rings of detectors, line-of-response events from a patient while the patient is moving in the PET scanner, at least some of the line-of-response events comprising random contribution;
    modeling, by a processor of a PET system, the random contribution as a product of transverse singles efficiencies with the plurality ring detectors treated as one ring along an axial direction;
    reducing, by the processor of the PET system, variance of the random contribution as a function of the modeling; and
    reconstructing, by the processor of the PET system, an image of the patient as a function of the reducing.

2. The method of claim 1 wherein acquiring comprises acquiring with the moving comprising continuous bed motion.

3. The method of claim 1 wherein modeling comprises modeling the random contribution to the line-of-response events as a Poisson variable.

4. The method of claim 1 wherein modeling comprises parameterizing the random contribution by radial and azimuth indexes, the radial and azimuth indexes defining a transverse direction, the random contribution comprising a sum of transversely spaced pairs of the detectors within a sinogram bin.

5. The method of claim 1 wherein modeling comprises decomposing the random contribution of the sinogram planes into the transverse singles efficiencies.

6. The method of claim 1 wherein modeling comprises mapping detector pairs for the random contribution to the one ring, the one ring comprising a virtual ring.

7. The method of claim 1 wherein reducing the variance comprises constraining the random contribution by the transverse singles efficiencies.

8. The method of claim 1 wherein reducing the variance comprises restoring axial efficiency from the transverse singles efficiencies and reducing axial variance as a function of the restored axial efficiency.

9. The method of claim 1 wherein reducing the variance comprises dividing the one ring into slices and scaling the random contribution axially as a smooth function over the slices.

10. The method of claim 1 wherein reconstructing comprises reconstructing from the line-of-response events corresponding to a mean random contribution of the modeling.

11. In a non-transitory computer readable storage medium having stored therein data representing instructions executable by a programmed processor of a positron emission tomography scanner for random sinogram variance reduction in continuous bed motion acquisition, the storage medium comprising instructions for:
    acquiring, with the positron emission tomography (PET) scanner having a plurality of rings of detectors, line-of-response events from a patient while the patient is moving in the PET scanner, at least some of the line-of-response events comprising random contribution;
    decomposing, by the programmed processor of the PET scanner, sinogram plane randoms into two-dimensional transverse efficiencies, the two-dimensional transverse efficiencies being transverse to an axial dimension, the sinogram plane randoms corresponding to the continuous bed motion acquisition by a bed of the PET scanner, with the plurality ring detectors treated as one ring along an axial direction;
    solving, by the programmed processor of the PET scanner, for a mean random sinogram from the transverse efficiencies; and
    smoothing, by the programmed processor of the PET scanner, variance of the sinogram plane randoms in the axial dimension as a function of the mean random sinogram.

12. The non-transitory computer readable storage medium of claim 11 wherein decomposing comprises decomposing plane by plane in a sinogram domain.

13. The non-transitory computer readable storage medium of claim 11 wherein decomposing comprises modeling the sinogram plane randoms as a Poisson variable and accounting for compression by parameters defined in the radial and azimuth dimensions and not the axial dimension.

14. The non-transitory computer readable storage medium of claim 11 wherein solving comprises iteratively estimating the transverse efficiencies.

15. The non-transitory computer readable storage medium of claim 11 wherein smoothing comprises smoothing by transverse segment.

16. The non-transitory computer readable storage medium of claim 11 wherein smoothing comprises constraining the sinogram plane randoms as a function of a product of the transverse efficiencies.

17. A system for random sinogram variance reduction in continuous bed motion acquisition, the system comprising:
    a bed configured to move during a positron emission tomography (PET) scan;

rings of detectors spaced axially operable to perform the PET scan while the bed moves; and a processor connected to the detectors, the processor configured to constrain random contribution to line-of-response events as a function of a product of efficiencies of the detectors, the product being transverse to an axial direction, with the plurality ring detectors treated as one ring along an axial direction.

18. The system of claim 17 wherein the processor is configured to constrain by iteratively solving for the efficiencies from a noisy random sinogram plane, the efficiencies comprising transverse efficiencies.

19. The system of claim 17 wherein the processor is configured to constrain by decomposing sinogram plane randoms into the efficiencies.

20. The system of claim 17 wherein the processor is configured to constrain by restoring axial information from the product.

21. The method of claim 1 wherein modeling comprises modeling with the transverse efficiencies and without singles.

* * * * *